United States Patent [19]

Thompson

[11] Patent Number: 4,595,533

[45] Date of Patent: Jun. 17, 1986

[54] METHOD FOR PRODUCING N-ORGANOCARBAMATES AND N,N-BIS(ORGANO)CARBAMATES

[75] Inventor: Ralph B. Thompson, Oakbrook, Ill.

[73] Assignee: PPG Industries, Inc., Pittsburgh, Pa.

[21] Appl. No.: 422,235

[22] Filed: Sep. 23, 1982

[51] Int. Cl.$^4$ ............... C07D 267/06; C07D 265/06
[52] U.S. Cl. ............... 260/239.3 R; 544/97; 548/229; 560/24; 560/157
[58] Field of Search ............... 560/24, 157; 260/239.3 R; 544/97; 548/229

[56] References Cited

U.S. PATENT DOCUMENTS 4,395,565  7/1983  Romano et al. ............... 560/24

OTHER PUBLICATIONS

Pauling, "General Chemistry", 3rd Edition, (1970), (Freeman), pp. 568 and 569.

*Primary Examiner*—Robert T. Bond
*Attorney, Agent, or Firm*—George D. Morris

[57] ABSTRACT

Esters of carbamic acids containing at least one hydrogen atom attached to the carbamic nitrogen atom are reacted with organic carbonates to produce esters of carbamic acids having a greater degree of organic substitution on the carbamic nitrogen atom than the reactant esters. Preferably, the reactant esters are alkylated using dialkyl carbonates.

27 Claims, No Drawings

METHOD FOR PRODUCING N-ORGANOCARBAMATES AND N,N-BIS(ORGANO)CARBAMATES

BACKGROUND OF THE INVENTION

N-Organocarbamates, also known as esters of N-organocarbamic acids, and N,N-bis(organo)carbamates, also known as esters of N,N-bis(organo)carbamic acids, are compounds of many uses. Various compounds within these classes are known to have utility as insecticides, acaricides, miticides, nematocides, fungicides, rodenticides, herbicides, plant growth regulators, animal repellants or pharmaceuticals.

It is frequently desired to convert an ester of a carbamic acid to an ester of a carbamic acid having a greater degree of organic substitution on the carbamic nitrogen atom than the original ester. It has now been discovered that many organic carbonates are useful to effect this conversion. Accordingly, the present invention is a method comprising reacting a first ester of a carbamic acid containing at least one hydrogen atom attached to the carbamic nitrogen atom thereof, with organic carbonate to produce a second ester of a carbamic acid having a greater degree of organic substitution on the carbamic nitrogen atom thereof than the first ester.

The organic carbonate used in the process is subject to wide variation and may be represented by the formula $$R_1OCOR_2 \quad \text{(I)}$$

wherein $R_1$ and $R_2$ are each independently monovalent organic groups which may be the same or different. The alpha carbon of at least one of $R_1$ and $R_2$ should be substantially sterically unhindered so that one of these groups may replace hydrogen of the carbamic nitrogen to form the second ester.

Typically $R_1$ is alkyl, alpha,beta-saturated alkenyl, aralkyl, (cycloalkyl)alkyl, cycloalkyl or lower aryl, and $R_2$ is alkyl, alpha,beta-saturated alkenyl, aralkyl or (cycloalkyl)alkyl.

When alkyl is employed, it usually has from 1 to about 20 carbon atoms, often from 1 to about 10 carbon atoms. Lower alkyl having from 1 to about 4 carbon atoms is preferred. Methyl and ethyl are especially preferred. The alpha,beta-saturated alkenyl used generally has from 3 to about 10 carbon atoms; allyl is preferred. When aralkyl is employed, the aryl portion generally contains from 6 to about 10 carbon atoms and the alkyl portion usually contains from 1 to about 10 carbon atoms; benzyl is preferred. When (cycloalkyl)alkyl is used, the cycloalkyl portion generally contains from about 6 to about 8 carbon atoms and the alkyl portion typically contains from 1 to about 10 carbon atoms; cyclohexylmethyl is preferred. The cycloalkyl typically has from about 6 to about 8 carbon atoms; cyclohexyl is preferred. The lower aryl usually has from 6 to about 10 carbon atoms; phenyl is preferred. These groups are usually unsubstituted, although one or more minor substituents which do not render the organic carbonate unsuitable for its intended purpose may be present on any of the groups. Similarly, those groups having one or more rings are usually homocyclic, but one or more hetero atoms may be present so long as they do not seriously interfere with formation of the second ester. The aliphatic groups and the aliphatic portions of hybrid groups such as aralkyl may be straight or branched, but it is preferred they be straight. Only one organic carbonate or a plurality of organic carbonates may be used as desired.

When a mixed organic carbonate, that is, an organic carbonate wherein $R_1$ and $R_2$ differ, is employed, the identity of the second ester product can be influenced by the relative degrees of steric hinderance of $R_1$ and $R_2$. In some cases substantially only one second ester is obtained; in others, mixtures of second esters result. However, the degree of steric hinderance of the alpha carbon atom of at least one of $R_1$ and $R_2$ should not be so great as to preclude formation of at least one second ester.

Examples of organic carbonates which may be employed include dimethyl carbonate, ethyl methyl carbonate, diethyl carbonate, propyl methyl carbonate, isopropyl methyl carbonate, isopropyl ethyl carbonate, butyl methyl carbonate, secondary-butyl methyl carbonate, isobutyl methyl carbonate, tertiary-butyl methyl carbonate, cyclohexyl methyl carbonate, benzyl methyl carbonate, phenyl methyl carbonate and diallyl carbonate. It is preferred that at least one of $R_1$ and $R_2$ be methyl or ethyl. The particularly preferred organic carbonates are dimethyl carbonate, diethyl carbonate and diallyl carbonate.

The first ester used in the process may be widely varied, and may be presented by the formula $$R_3OCN-R_4 \quad \text{(II)}$$
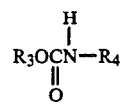

wherein $R_3$ is a monovalent organo group, $R_4$ is hydrogen or a monovalent organo group, or $R_3$ and $R_4$ taken together constitute a bivalent organo group. Substantially any monovalent organo groups which do not preclude formation of the second ester may be used for $R_3$ and $R_4$. Similarly, substantially any bivalent organo group which does not preclude formation of the second ester may be used for $R_3$ and $R_4$ taken together. They may be simple or they may be highly complex. Examples of monovalent organo groups which may be used include alkyl, alkenyl, aryl, (cycloalkyl)alkyl, aralkyl and cycloalkyl. Such groups may be substituted or unsubstituted. They may themselves be inert to the conditions of the reaction or they may contain groups, such as mercapto, hydroxyl, amino or selenyl, which may be reactive with organic carbonate. When an aryl group or a group containing an aryl portion is used, it may be homocyclic or heterocyclic; it may comprise a single ring or it may comprise a ring assembly. Examples of bivalent organo groups that may be used include alkylene, alkenylene, alkapolyenylene or more complex hybrid groupings as for example those comprising arylene and alkylene and those comprising cycloalkylidene and alkylene. Such groups may be substituted or unsubstituted. They may contain within the ring structure other atoms as well as carbon atoms; examples include oxygen, sulfur, nitrogen and selenium. They may contain functional groups such as for example, keto groups, mercapto groups, lactone groups or lactam groups. They may themselves be inert to the conditions of the reaction or they may contain groups which may be reactive with organic carbonate. When a grouping containing an arylene portion is used, it may be homocyclic or heterocyclic; it may comprise a single ring or it may comprise a ring assembly.

Included within the broad class of first esters are the following subclasses:

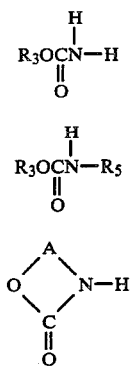

wherein $R_3$ is as discussed above; $R_5$ is a monovalent organo group as discussed above, but not hydrogen; and A is a bivalent organo group as discussed above wherein $R_3$ and $R_4$ are taken together. Usually A contains from about 2 to about 4 carbon atoms.

Only one first ester may be employed or a plurality of such materials may be used, as desired.

When one or more esters of Formula III are employed in the reaction, either or both hydrogen atoms on the carbamic nitrogen may be replaced depending upon such factors as the identities of the reactants, proportions of reactants, temperature, pressure and catalyst used, if any.

The reaction of the first ester with organic carbonate is usually conducted in the liquid phase. It may be carried out batchwise, continuously, semibatchwise or semicontinuously. When the organic carbonate is a liquid under the conditions of the reaction, it often acts as a solvent for the first ester. Typically, but not necessarily, excess organic carbonate is employed and this usually serves to dissolve the first ester throughout the reaction. In many cases, one or more by-products of the reaction, most notably alcohols, also tend to dissolve the first ester. Although extrinsic solvent is not ordinarily employed, it may be used when desired or when necessary to dissolve one or more of the reactants. Examples of suitable extrinsic solvents include methanol, ethanol, acetonitrile, benzene, toluene, dioxane, dimethylformamide and chlorinated solvents such as chloroform, methylene chloride, ethylene chloride, carbon tetrachloride and chlorobenzene. Only one extrinsic solvent or a plurality of extrinsic solvents may be used as desired. For many reactions, extrinsic solvent need not be introduced and the reaction may be neat.

When extrinsic solvent is used, the weight ratio of extrinsic solvent to the first ester initially present is subject to wide variation. Generally, the amount of solvent should be sufficient to dissolve the reactants at the reaction temperature. The weight ratio of extrinsic solvent, when used, to the first ester initially present is usually in the range of from about 0.01:1 to about 20:1. From about 0.1:1 to about 5:1 is preferred.

The temperatures at which the reaction is conducted may vary considerably, but ordinarily they are in the range of from about 100° C. to about 250° C. Temperatures in the range of from about 130° C. to about 220° C. are preferred.

The pressures at which the reaction is conducted are similarly susceptible to wide variation. Atmospheric and superatmospheric pressures are generally employed, although subatmospheric pressures may sometimes be used. Generally the pressure is in the range of from about zero to about 7500 kilopascals, gauge, but higher pressures may be used. Preferably the pressure is in the range of from about 500 to about 3500 kilopascals, gauge. Frequently, autogenous pressure is used.

The reaction may be conducted in the presence of catalyst although in many instances the use of catalyst is often not needed. Exemplary catalysts which may be used include nitrogen-containing heterocyclic catalysts such as pyridine, 4-(dimethylamino)pyridine, imidazole, 2,6-lutidine and 2,4,6-collidine. Only a single catalyst or a mixture of catalysts may be used where desired. The preferred catalyst is 4-(dimethylamino)pyridine. Other exemplary catalysts include tertiary amines such as triethyl amine.

The equivalent ratio of the catalyst, when used, to the first ester initially present may vary widely, but ordinarily it is in the range of from about 0.005:1 to about 0.5:1. It is preferred that the equivalent ratio be in the range of from about 0.01:1 to about 0.2:1.

Following preparation, the second ester may be recovered from the reaction mixture by any of the various techniques known to the art. Distillation at reduced pressure is one such technique that is frequently employed.

The present invention is especially useful for the alkylation of esters of carbamic acid having no substituents on the carbamic nitrogen atom and/or N-organocarbamates. In such cases at least one of $R_1$ and $R_2$ in Formula I, above, is alkyl. Dialkyl carbonates are preferred for these alkylations.

The invention is further described in conjunction with the following example which is to be considered illustrative rather than limiting.

EXAMPLE

A one-liter reactor equipped with an agitator, a thermometer, a pressure gauge and an electric heating mantle was charged with 8 grams of methyl carbamate and 150 milliliters of dimethyl carbonate. The reactor was sealed and heated. The temperatures and pressures at various times after heating was initially begun are shown in Table 1.

TABLE 1

| Time, Hours:Minutes | Temperature, °C. | Pressure, Kilopascals, Gauge | Remarks |
|---|---|---|---|
| 0:00 | Ambient | 0 | Heat On |
| 0:22 | 135 | 414 | |
| 0:35 | 155 | 689 | |
| 0:58 | 175 | 965 | |
| 1:26 | 180 | 1000 | |
| 2:23 | 180 | 1103 | |
| 2:37 | 180 | 1103 | |
| 3:45 | 180 | 1103 | Heat Off |

The reactor was then allowed to cool overnight to ambient temperature. A sample of gas taken from the reactor was found to contain carbon dioxide. The pressure was brought to ambient and the reactor was found to contain 162.4 grams of liquid. Gas-liquid chromatographic analysis of the liquid showed it to contain 80 area percent dimethyl carbonate, 9 area percent methanol, 6.2 area percent methyl carbamate, and 3.5 area percent methyl N-methylcarbamate.

The reactor was charged with 157 grams of the above liquid, sealed and heated. The temperatures and pressures at various times after heating was begun are shown in Table 2.

TABLE 2

| Time, Hours:Minutes | Temperature, °C. | Pressure, Kilopascals, Gauge | Remarks |
|---|---|---|---|
| 0:00 | Ambient | 0 | Heat On |
| 0:55 | 175 | 1413 | |
| 1:08 | 205 | 2310 | |
| 1:27 | 205 | 2206 | |
| 2:14 | 205 | 2206 | |
| 2:55 | 205 | 2758 | |
| 4:00 | 205 | 3034 | Heat Off |

A sample of liquid was withdrawn from the reactor and analyzed by gas-liquid chromatography. The analysis showed the liquid to contain 59 area percent dimethyl carbonate, 16.5 area percent methanol, 7.0 area percent methyl N-methylcarbamate and 6.3 area percent of material believed to be methyl N,N-dimethylcarbamate. No methyl carbamate was detected.

Although the present invention has been described with reference to specific details of certain embodiments thereof, it is not intended that such details should be regarded as limitations upon the scope of the invention except insofar as they are included in the accompanying claims.

I claim:

1. A method comprising reacting a first ester of a carbamic acid containing at least one hydrogen atom attached to the carbamic nitrogen atom thereof, with organic carbonate to produce a second ester of a carbamic acid having a greater degree of organic substitution on the carbamic nitrogen atom thereof than said first ester.

2. The method of claim 1 wherein said organic carbonate is represented by the formula

wherein $R_1$ and $R_2$ are each independently monovalent organic groups which may be the same or different.

3. The method of claim 2 wherein $R_1$ is alkyl, alpha,beta-saturated alkenyl, aralkyl, (cycloalkyl)alkyl, cycloalkyl or lower aryl, and $R_2$ is alkyl, alpha,beta-saturated alkenyl, aralkyl or (cycloalkyl)alkyl.

4. The method of claim 2 wherein
   a. $R_1$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from 1 to about 10 carbon atoms, (cycloalkyl)alkyl wherein the cycloalkyl portion contains from about 6 to about 8 carbon atoms and the alkyl portion contains from 1 to about 10 carbon atoms, cycloalkyl having from about 6 to about 8 carbon atoms, or lower aryl having from 6 to about 10 carbon atoms; and
   b. $R_2$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from one to about 10 carbon atoms, or (cycloalkyl)alkyl wherein the cycloalkyl portion contains from about 6 to about 8 carbon atoms and the alkyl portion contains from 1 to about 10 carbon atoms.

5. The method of claim 2 wherein $R_1$ and $R_2$ are each independently alkyl having from 1 to about 10 carbon atoms.

6. The method of claim 2 wherein $R_2$ is methyl.

7. The method of claim 2 wherein $R_2$ is ethyl.

8. The method of claim 1 wherein said organic carbonate is dimethyl carbonate.

9. The method of claim 1 wherein said organic carbonate is diethyl carbonate.

10. The method of claim 1 wherein said organic carbonate is diallyl carbonate.

11. The method of claim 1 wherein 4-(dimethylamino)pyridine is used as catalyst.

12. The method of claim 1 wherein pyridine is used as catalyst.

13. The method of claim 1 wherein the equivalent ratio of 4-(dimethylamino)pyridine) to said first ester thereof initially present is in the range of from about 0.005:1 to about 0.5:1.

14. The method of claim 1 wherein the equivalent ratio of pyridine to said first ester thereof initially present is in the range of from about 0.005:1 to about 0.5:1.

15. The method of claim 1 wherein said reaction is conducted at a temperature in the range of from about 100° C. to about 250° C.

16. The method of claim 1 wherein said reaction is conducted at a pressure in the range of from about zero to about 7500 kilopascals, gauge.

17. The method of claim 1 wherein said reaction is conducted in the presence of solvent.

18. The method of claim 17 wherein the weight ratio of said solvent to said first ester initially present is in the range of from about 0.01:1 to about 20:1.

19. The method of claim 1 wherein said reaction is neat.

20. The method of claim 1 wherein said first ester is represented by the formula

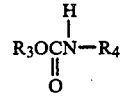

wherein $R_3$ is a monovalent organo group, $R_4$ is hydrogen or a monovalent organo group, or $R_3$ and $R_4$ taken together constitute a bivalent organo group.

21. The method of claim 1 wherein said first ester is represented by the formula

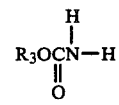

wherein $R_3$ is a monovalent organo group.

22. The method of claim 1 wherein said first ester is represented by the formula

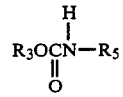

wherein $R_3$ is a monovalent organo group and $R_5$ is a monovalent organo group.

23. The method of claim 1 wherein said first ester is represented by the formula

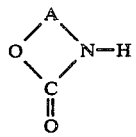

wherein A is a bivalent organo group.

24. A method comprising reacting a first ester of a carbamic acid represented by the formula

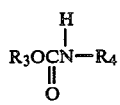

wherein $R_3$ is a monovalent organo group, $R_4$ is hydrogen or a monovalent organo group, or $R_3$ and $R_4$ taken together constitute a bivalent organo group, with organic carbonate represented by formula

wherein $R_1$ and $R_2$ are each independently monovalent organic groups which may be the same or different, to produce a second ester of a carbamic acid having a greater degree of organic substitution on the carbamic nitrogen atom thereof than said first ester.

25. The method of claim 24 wherein
   a. $R_1$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from 1 to about 10 carbon atoms, (cycloalkyl)alkyl wherein the cycloalkyl portion contains from about 6 to about 8 carbon atoms and the alkyl portion contains from 1 to about 10 carbon atoms, cycloalkyl having from about 6 to about 8 carbon atoms, or lower aryl having from 6 to about 10 carbon atoms; and
   b. $R_2$ is alkyl having from 1 to about 20 carbon atoms, alpha,beta-saturated alkenyl having from 3 to about 10 carbon atoms, aralkyl wherein the aryl portion contains from 6 to about 10 carbon atoms and the alkyl portion contains from one to about 10 carbon atoms, or (cycloalkyl)alkyl wherein the cycloalkyl portion contains from about 6 to about 8 carbon atoms and the alkyl portion contains from 1 to about 10 carbon atoms.

26. The method of claim 25 wherein either
   a. $R_3$ is alkyl, alkenyl, aryl, (cycloalkyl)alkyl, aralkyl or cycloalkyl and $R_4$ is hydrogen, alkyl alkenyl, aryl, (cycloalkyl)alkyl, aralkyl or cycloalkyl; or
   b. $R_3$ and $R_4$ taken together constitute alkylene, alkenylene, alkapolyenylene, a bivalent organo group comprising arylene and alkylene, or a bivalent organo group comprising cycloalkylidene and alkylene.

27. The method of claim 26 wherein said organic carbonate is dimethyl carbonate, diethyl carbonate, or diallyl carbonate.

* * * * *

UNITED STATES PATENT AND TRADEMARK OFFICE
CERTIFICATE OF CORRECTION

PATENT NO. : 4,595,533

DATED : June 17, 1986

INVENTOR(S) : Ralph B. Thompson

It is certified that error appears in the above-identified patent and that said Letters Patent are hereby corrected as shown below:

Claim 13, Column 6, line 20, "1" should be --11--;

Column 6, line 21, "4-(dimethylamino)pyridine)" should be --4-(dimethylamino)pyridine;

Claim 14, Column 6, line 24, "1" should be -- 12 --.

Signed and Sealed this

Third Day of February, 1987

Attest:

DONALD J. QUIGG

Attesting Officer

Commissioner of Patents and Trademarks